United States Patent [19]

Okazaki

[11] Patent Number: 4,611,340

[45] Date of Patent: Sep. 9, 1986

[54] APPARATUS FOR EXAMINING A BIOLOGICAL OBJECT BY USING RADIATION

[75] Inventor: Kiyoshi Okazaki, Tochigi, Japan

[73] Assignee: Kabushiki Kaisha Toshiba, Kawasaki, Japan

[21] Appl. No.: 611,150

[22] Filed: May 17, 1984

[30] Foreign Application Priority Data

May 20, 1983 [JP] Japan .................. 58-88952

[51] Int. Cl.⁴ .................. A61B 6/00; H04N 5/32; H05G 1/10
[52] U.S. Cl. .................. 378/95; 128/708; 358/111; 378/99
[58] Field of Search ............ 378/95, 99, 8; 128/708, 128/709; 358/111

[56] References Cited

U.S. PATENT DOCUMENTS 3,520,295  7/1970  Kelly .................. 378/95
4,204,225  5/1980  Mistretta .................. 358/111
4,204,226  5/1980  Mistretta et al. .................. 358/111

Primary Examiner—Bruce C. Anderson
Assistant Examiner—T. N. Grigsby
Attorney, Agent, or Firm—Finnegan, Henderson, Farabow, Garrett & Dunner

[57] ABSTRACT

In an angiographic apparatus, operation timings of an entire system, e.g., an X-ray generator, an X-ray detector, a transmission image processor, and an injector for X-ray contrast medium are controlled in synchronism with cardiac beat waves of a biological object.

4 Claims, 14 Drawing Figures

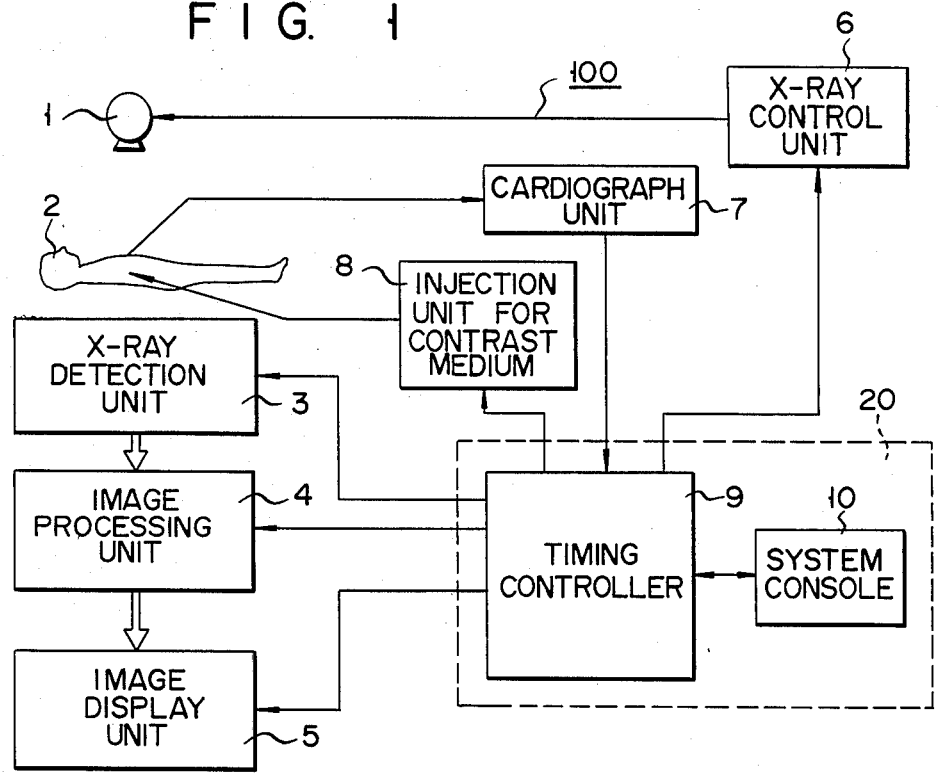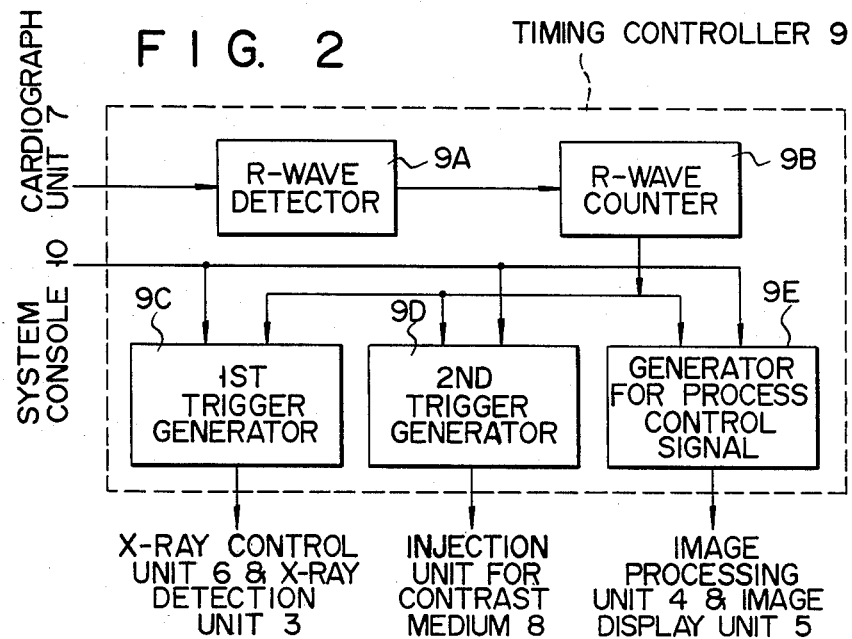

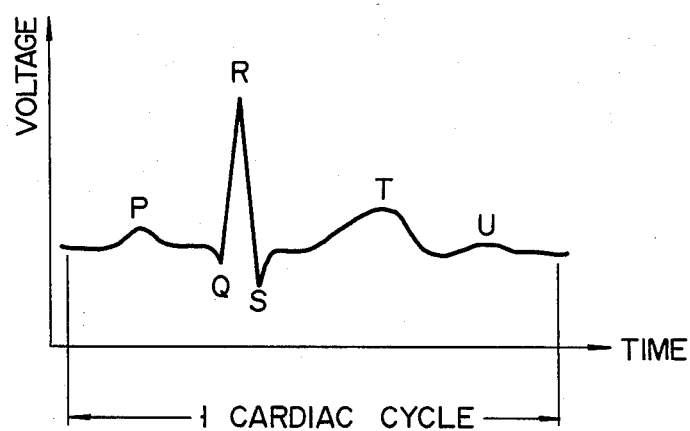
F I G. 3

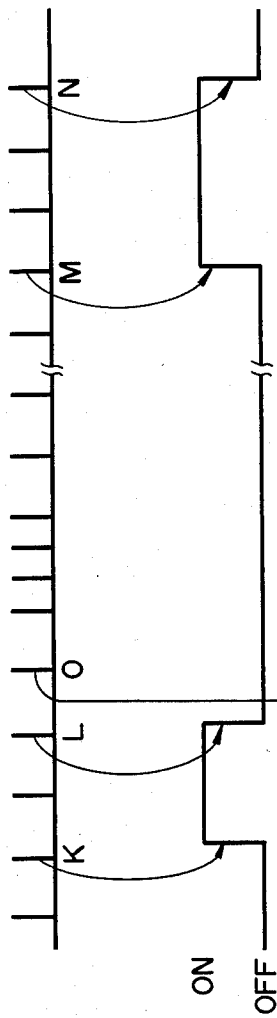
FIG. 4A R-WAVE BEAT NUMBER
FIG. 4B X-RAY PROJECTION
FIG. 4C INJECTION FOR CONTRAST MEDIUM
FIG. 4D CONCENTRATION OF CONTRAST MEDIUM

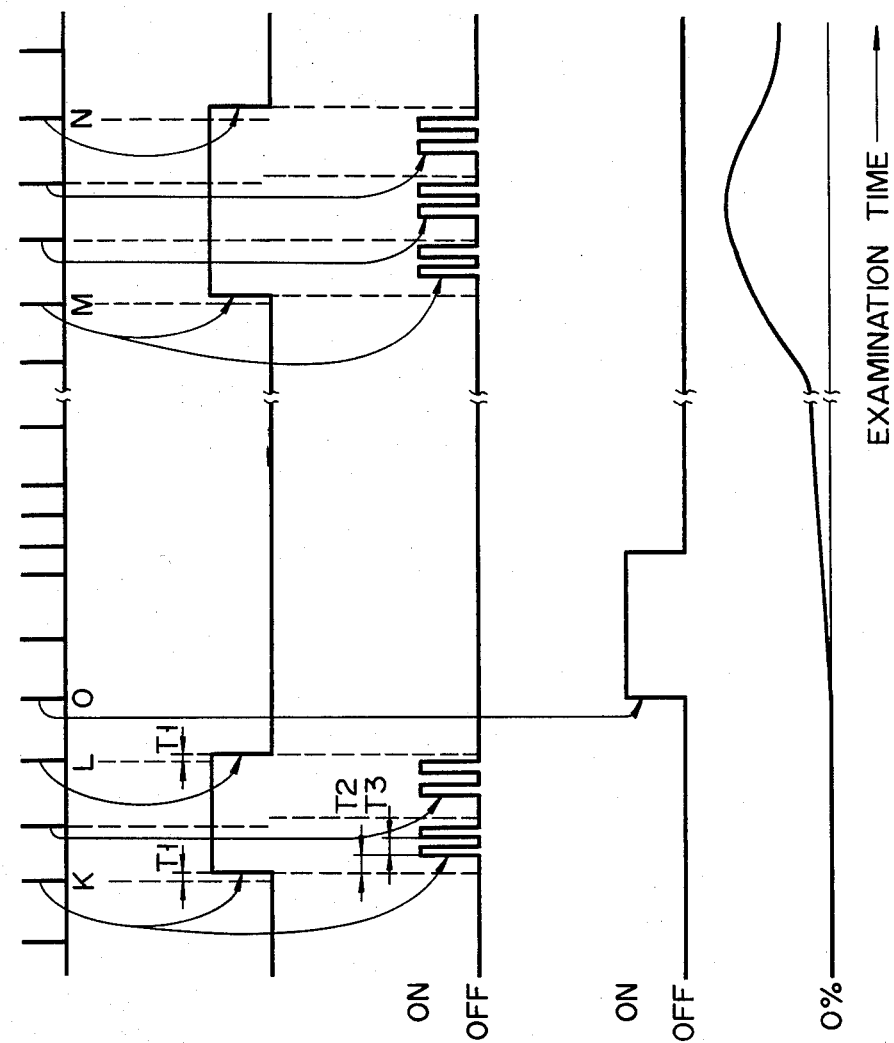

APPARATUS FOR EXAMINING A BIOLOGICAL OBJECT BY USING RADIATION

BACKGROUND OF THE INVENTION

1. Field of the Invention

The present invention relates to an apparatus for examining a biological object by using radiation in which angiography can be effected in synchronism with the cardiac beat waves of the biological object.

2. Description of the Prior Art

In the conventional radiation diagnostic apparatus, for example, in the X-ray diagnostic apparatuses disclosed in U.S. Pat. Nos. 4,204,225 and 4,204,226, etc., the timing of the angiography of the circulatory organs, such as the blood vessels and the heart, are determined on the basis of predetermined times. That is, to obtain the mask images for a biological object (hereinbelow, simply referred to as an object) before an X-ray contrast medium reaches a predetermined portion of the object, e.g., a patient on the basis of the instant ($T_0$) at which the injection or administration of the X-ray constrast medium commences, the X-ray is projected, or irradiated for ($S_1$) seconds immediately after ($T_1$) seconds have passed from the above instant ($T_0$). Subsequently the X-ray is again projected for ($S_2$) seconds immediately after ($T_2$) seconds have passed from the instant ($T_0$), thereby obtaining the contrast images of the object when the X-ray contrast medium reached the predetermined portion. In the case of using the pulsatory X-ray as the X-ray to be projected, pulse repetition rates $PD_1$ and $PD_2$ and pulse numbers $PN_1$ and $PN_2$ are substituted for the above projection times $S_1$ and $S_2$. These new projection times $S_1$ and $S_2$ are represented by the following equations.

$$S_1 = PD_1 \times PN_1$$

$$S_2 = PD_2 \times PN_2$$

The mask images are digitally subtracted from the contrast images obtained in this way, so that the subtraction images with respect to only the diagnostic portion, e.g., blood vessels into which the X-ray contrast medium has been injected, are obtained and displayed.

On the other hand, the time period when the blood circulates, i.e., the time period when the X-ray contrast medium flows, does not depend on the above-described time, for example, the projection time, but depends upon the beat numbers of the patient. However, in the conventional angiographic apparatus, the timings are set entirely regardless of the blood circulating time depending upon the beat numbers of the biological object. Therefore, in the conventional X-ray diagnostic apparatus, the timings of X-ray projection are usually shifted with respect to the distribution of the X-ray contrast medium so that this causes a problem such that the contrast images are not collected at the moment the X-ray contrast medium appears with the highest concentration in the portions to be diagnosed. In addition, if the X-ray is continuously projected for a long time to solve this problem, there will also be a drawback of exposing the object to an excessive amount of X-rays during examination. Consequently, this also causes a danger of an increase in exposure dosage. On the other hand, if the digital subtraction is effected between the images obtained at different phases of the cardiac beat according to the timing setting irrespective of the beat numbers, there occurs an artifact in the subtraction images due to phase deviation of the cardiac beat. As a result, this artifact can make accurate diagnosis difficult.

The present invention is made in consideration of such circumstances and intends to provide an apparatus for examining a biological object by using radiation, in which by projecting the radiation and by collecting image data at timings based on the circulation rate of the blood, i.e., in synchronism with the cardiac beat or, heart beat, the exposure dosage to the object can be reduced as small as possible, and at the same time the diagnostic iamges with high picture quality can be displayed, thereby enabling the accurate diagnosis to be performed.

SUMMARY OF THE INVENTION

The objects and features of the present invention may be realized by providing an apparatus for examining a biological object by using radiation comprising means for generating radiation, means for controlling the radiation generating means so as to irradiate the radiation toward the biological object at a predetermined time period, means for detecting the radiation which has been transmitted through the biological object and for producing a radiation transmission image thereof as a digital image signal, means for processing a plurality of digital image signals in a digital subtraction method so as to obtain a plurality of subtraction image signals, means for displaying at least a subtraction image of the biological object obtained from the subtraction image signal, means for measuring cardiac beat waves of the biological object, means for administrating a radiation contrast medium into the biological object, and system control means for performing at least timing controls of the apparatus in synchronism with the cardiac beat waves of the biological object as a reference signal.

BRIEF DESCRIPTION OF THE DRAWINGS

For a better understanding of these and other objects and features of the invention, reference is made to the following detailed description of the invention to be read in conjunction with the following drawings, wherein:

FIG. 1 is a schematic diagram of an X-ray diagnostic apparatus according to one preferred embodiment of the present invention;

FIG. 2 is a block diagram of an internal circuit of a timing controller shown in FIG. 1;

FIG. 3 shows an electrocardiogram;

FIGS. 4A–4D show timing charts for the operation of the apparatus shown in FIG. 1;

FIGS. 7A to 7E show timing charts for the operation of a pulsatory X-ray diagnostic apparatus according to the second preferred embodiment.

DETAILED DESCRIPTION OF THE PREFERRED EMBODIMENT

Figure 5:
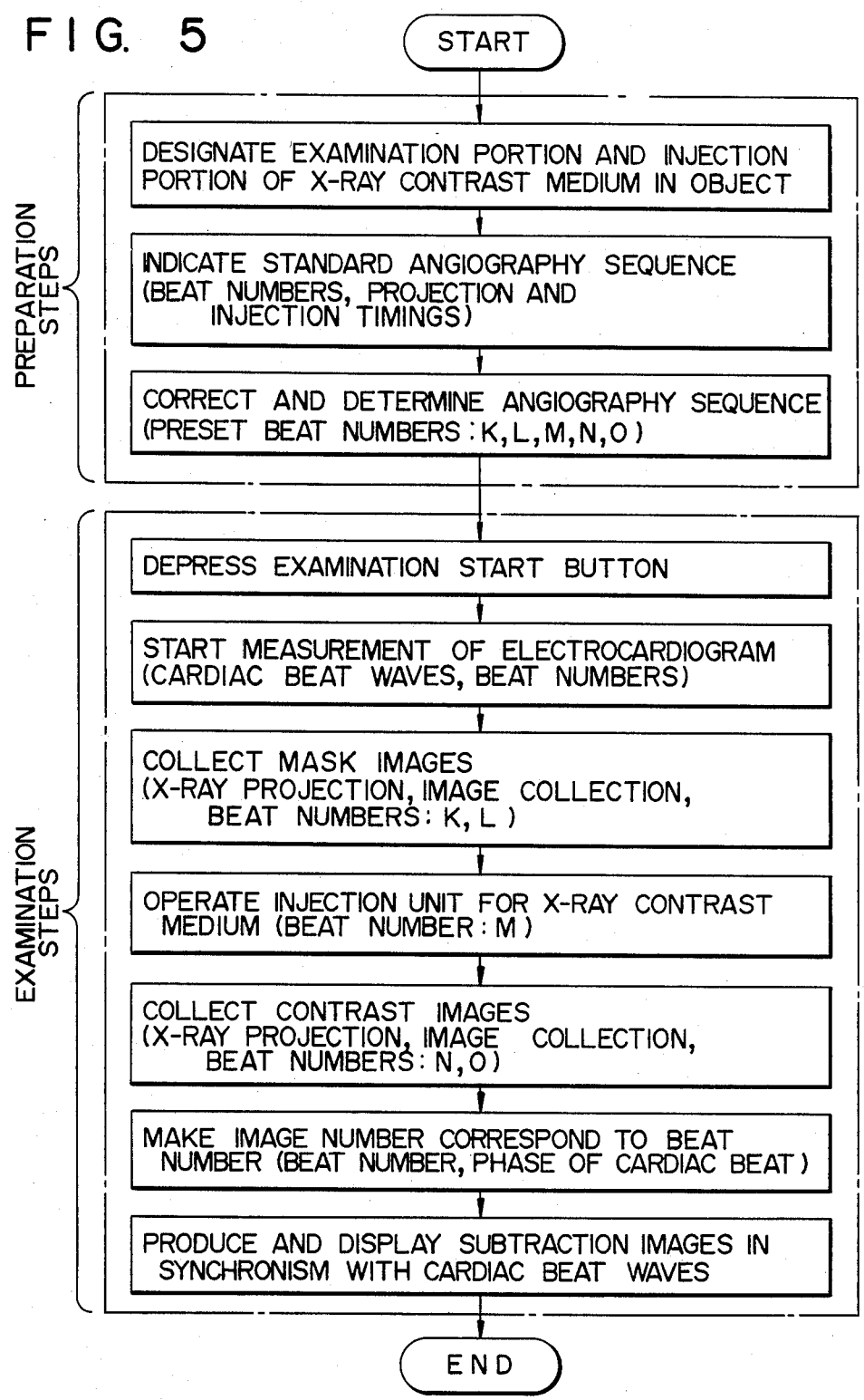
FIG. 5 shows a flow chart for the operation of the apparatus shown in FIG. 1.

Before proceeding with the various types of preferred embodiments, a principle idea of the present invention will now be explained.

The timing of the entire system, e.g., the timing of the X-ray projection, the timing of the administration of the X-ray contrast medium, and the timing of the signal processing, are all controlled in synchronism with the cardiac beat, or heart beat of the patient.

One embodiment of the present invention will now be described with reference to the drawings.

FIG. 1 shows a block diagram showing an apparatus for examining a biological object using radiation, e.g., an X-ray diagnostic apparatus 100, as one embodiment of the present invention.

In FIG. 1, an X-ray generation unit (e.g., an X-ray tube) 1 generates, or irradiates an X-ray continuously upon the biological object 2 under investigation, for example, a patient or the like. An X-ray detection unit 3 detects the X-ray transmission image from the biological object 2, e.g., a patient (referred to as the object) and converts it into an analog signal. This detection unit 3 comprises, for example, at least: an image intensifier for transforming the X-ray transmission image into an optical image; an optical system for adjusting the amount of light on the optical image; and an image pickup tube for transforming the optical image into an analog signal (video signal). An image processing unit 4 comprises, at least: an A/D converter for converting the analog signal which is output from the X-ray detection unit 3 into the digital signal; an image processor for executing the extraction of a profile of predetermined portion in the image, arithmetic operation in the image such as the calculation of the size of an area, and arithmetic operation between the images, such as the digital subtraction of the mask image from the contrast image; and an image memory for storing the image signal obtained by the X-ray projection and the image signal obtained after the arithmetic operation processing between the images. An image display unit 5 comprises, at least: a D/A converter for converting the digital signal (image data signal) to be output from the image processing unit 4 into the analog signal; and a TV monitor for displaying the analog signal as a diagnostic iamge. An X-ray control unit 6 controls the intensity and projection time of the X-ray of the X-ray tube 1. A cardiograph unit 7, which includes an A/D converter therein, serves to measure the electrocardiogram of the object 2 and to output a digital data signal to a system control unit 20 which will be described later. An injection unit 8 for X-ray contrast medium serves to inject the X-ray contrast medium of a predetermined quantity into the object 2 at given instants under control of a system control unit 20. The system control unit 20 is composed of a timing controller 9 and a system console 10. The timing controller 9 controls all timings of the X-ray detection unit 3, image processing unit 4, image display unit 5, X-ray control unit 6, and injection unit 8 for the X-ray contrast medium on the basis of the digital data signal which is output from the cardiograph unit 7. A system console 10 can select and designate through a keyboard (not shown in detail) the angiographic conditions, photographic sequence and image processing mode in accordance with the portion under investigation in the object 2 and with the position where the X-ray contrast medium is injected which have been preliminarily programmed and stored in the timing controller 9. Namely, the system control unit 20 can control the whole system.

Generally, as shown in FIG. 3, P-, Q-, R-, S-, T-, and U-waves are included in one cardiac cycle (, or heart cycle) of the electrocardiogram. The R-wave among these waves has the features of having the largest amplitude and of not being relatively influenced by the disease condition of the patient. Therefore, this embodiment uses this R-wave as a reference signal of the system. In other words, the timing control of the entire system is performed on the basis of this R-wave. Namely, the operation timings of the entire system are controlled in synchronizm with the cardiac beat wave, e.g., the R-wave of the electrocardiogram.

As shown in FIG. 2, the timing controller 9 comprises: an R-wave detector 9A which receives the electrocardiogram of the object 2 derived from the cardiograph unit 7 and detects the R-waves in the cardiac beat waves by, for instance, a threshold level circuit; an R-wave counter 9B for counting the number of R-waves detected by the R-wave detector 9A; a first trigger generator 9C for outputting trigger signals which start and end the operations of the X-ray control unit 6 and X-ray detection unit 3, respectively, when the number of R-waves counted by the R-wave counter 9B reaches a number which has been preset in the system console 10; a second trigger generator 9D for outputting trigger signals which commence and terminate the operations of the injection unit 8 for the X-ray contrast medium when the number of R-waves reaches a preset number by the system console 10; and a generator for process control signal 9E which outputs a process control signal to instruct the start and end of predetermined operations of the image processing unit 4 and image display unit 5, respectively, when the number of the R-waves counted by the R-wave counter 9B reaches a preset number by the system console 10.

The system console 10 is constituted so that it can display on its built-in TV monitor a concentration curve of the X-ray contrast medium which can be preset as a standard curve with respect to the combination of the portion under investigation and the portion where the X-ray contrast medium is administrated, the beat number for determining the timing to collect the mask images before the X-ray contrast medium is injected, the beat number for determining the timing to collect the contrast images when the X-ray contrast medium reaches a predetermined portion, and the beat number for determining the timing to inject the X-ray contrast medium. Further the system console 10 enables the operator to interpret and manipulate the beat numbers.

Furthermore, when the image processing unit 4 receives the process control signal from the timing controller 9, it may select the optimum pair of the mask image and contrast image of which the phases of cardiac beat waves best coincide with that of the mask images. A plurality of mask images are obtained before the X-ray contrast medium reaches the predetermined portion and a plurality of contrast images are obtained after the contrast medium reached the predetermined portion. Then, it performs the digital subtraction between the contrast image and the mask image, thereby producing the subtraction images of which the background was removed and which consists of only the desirable portion, e.g., blood vessels where the X-ray contrast medium exists. After it has once stored the above subtraction images, it outputs the subtraction images continuously or at given intervals to the image display unit 5.

The operations of the above-described apparatus will then be described with reference to a timing chart of FIG. 4 and a flow chart of FIG. 5.

A preparation operation will be first explained. That is, the beat numbers of the cardiac beat waves, i.e., the R-wave, to specify desirable timings of X-ray exposure and of X-ray contrast medium are designated in the manner as follows by the system console 10. Namely, a preliminary stored data list relating to the portions under investigation and the portions where the X-ray contrast medium is injected, is displayed first on the built-in TV monitor in the system console 10. Then, desirable diagnostic portion and contrast medium injection portion are designated through the keyboard by the operator. For example, when the operator inputs the left heart system as the desirable diagnostic portion and inputs the superior vena cava as the desired portion where the X-ray contrast medium is to be injected, the system console 10 displays on the built-in TV monitor the standard concentration curve showing how the X-ray contrast medium set with regard to the input data, the beat number to determine the timing needed to collect various kinds of images, and the beat number to determine the timing needed to inject the X-ray contrast medium. Subsequently, the operator decides whether the set data is proper or not. If the various set values displayed on the TV monitor are improper, the operator appropriately corrects again the set values displayed on the TV monitor through the keyboard. In this way, the various beat numbers which will become the bases when the timings are set are input and stored by the system console 10 in accordance with the operator's discretion.

The preparation operation has been accomplished by the foregoing series of operations.

Next, the examination operation will commence.

The preset beat numbers K, L, ... N are designated as follows (see FIG. 4). Namely, they are defined by the intervals from the start of the administration of the X-ray contrast medium to the time when the contrast medium reaches the portion to be photographed. These intervals have been predetermined from clinical statistics.

The cardiograph unit 7 has already sequentially output the electrocardiogram data of the object 2 under investigation to the timing controller 9 of the system control unit 20. Upon completion of the preparation operation for the examination, the operator immediately starts the examination by pressing the examination start button (not shown) on the keyboard. In response to this input, the R-wave detector 9A in the timing controller 9 starts to detect the R-waves in the electrocardiogram data. Furthermore, the number of R-waves is counted by the R-wave counter 9B.

When the number of R-waves counted by the R-wave counter 9B coincides with the first beat number "K" which has been preset by the system console 10 (this comparison detection is performed by a comparator in the first trigger generator 9C, see FIG. 4A), the trigger signals are output from the first trigger generator 9C to the X-ray control unit 6 and X-ray detection unit 3. At the same time, the process control signal is also output from the process control signal generator 9E to the image processing unit 4. When the trigger signal and process control signal are output, in synchronizm with the first beat number "K", the continuous X-ray is projected, or irradiated from the X-ray tube 1 to the object 2 under control of the X-ray control unit 6 (see FIG. 4B). The X-ray transmitted through the object 2 is converted into a digital video signal by the X-ray detection unit 3 to which the process control signal has been supplied. Then the video signal is output to the image processing unit 4. The image processing unit 4 stores a number of images for each phase of the input video signal using the R-wave as the reference signal, i.e., the sync signal. It memorizes these images as a plurality of mask images before injecting the X-ray contrast medium. The ends of the X-ray projection and image storage are specified in response to the first trigger signal which is output from the first trigger generator 9C when the number of R-waves counted by the R-wave counter 9B becomes the second beat number "L" which has been preset by the system console 10.

Then, when the number of R-waves counted by the R-wave counter 9B coincides with the third beat number "O" which has been preset by the system console 10 as shown in FIG. 4C, the second trigger signal is output from the second trigger generator 9D to the X-ray contrast medium injection unit 8, so that the X-ray contrast medium is injected into the object 2 for a given time period. Therefore, when the given delay time which is specified by the beat number has passed after this X-ray contrast medium had been injected, the concentration of X-ray contrast medium in the desirable diagnostic portion gradually increases (see FIG. 4D).

After the injection of the X-ray contrast medium, when the number of R-waves counted by the R-wave counter 9B coincides with the fourth beat number "M" preset by the system console 10 (see FIG. 4A), the first trigger signals are output from the first trigger generator 9C to the X-ray control unit 6 and the X-ray detection unit 3. At the same time, the process control signal is also output from the process control signal generator 9E to the image processing unit 4. As explained above, when the first trigger signal and process control signals in synchronizm with the fourth beat number "M" are output, a continuous X-ray is once again projected from the X-ray tube 1 to the object 2 under control of the X-ray control unit 6. The X-ray image transmitted through the object 2 is converted into a digital video signal by the X-ray detection unit 3, and the resultant video signal is output to the image processing unit 4. The process control signals are input from the generator for process control signal 9E to these units 3 and 4. The image processing unit 4 stores a number of images at each phase of the electrocardiogram from the input video signal, using the R-wave as the reference signal. It memorizes these images as a plurality of contrast images after the X-ray contrast medium has reached the predetermined portion. Furthermore, the image processing unit 4 selects the mask image having the same phase as that of a number of contrast images from among the mask image group which have been already stored using the R-wave as the reference signal in response to the process control signal. Then, it performs the digital subtraction between the contrast images at the same phase and the mask image, thereby producing the subtraction images in which the background has been removed. After these subtraction images were once stored, the subtraction images are output continuously or at given intervals to the image display unit 5. The image display unit 5 displays the subtraction images as the diagnostic images on the TV monitor.

Although the foregoing embodiment related to the X-ray diagnostic apparatus 100 which stores the images of the object by projecting the continuous X-ray, an X-ray diagnostic apparatus which projects the pulsatory X-ray will be then described hereinbelow as a second embodiment.

Figure 6:
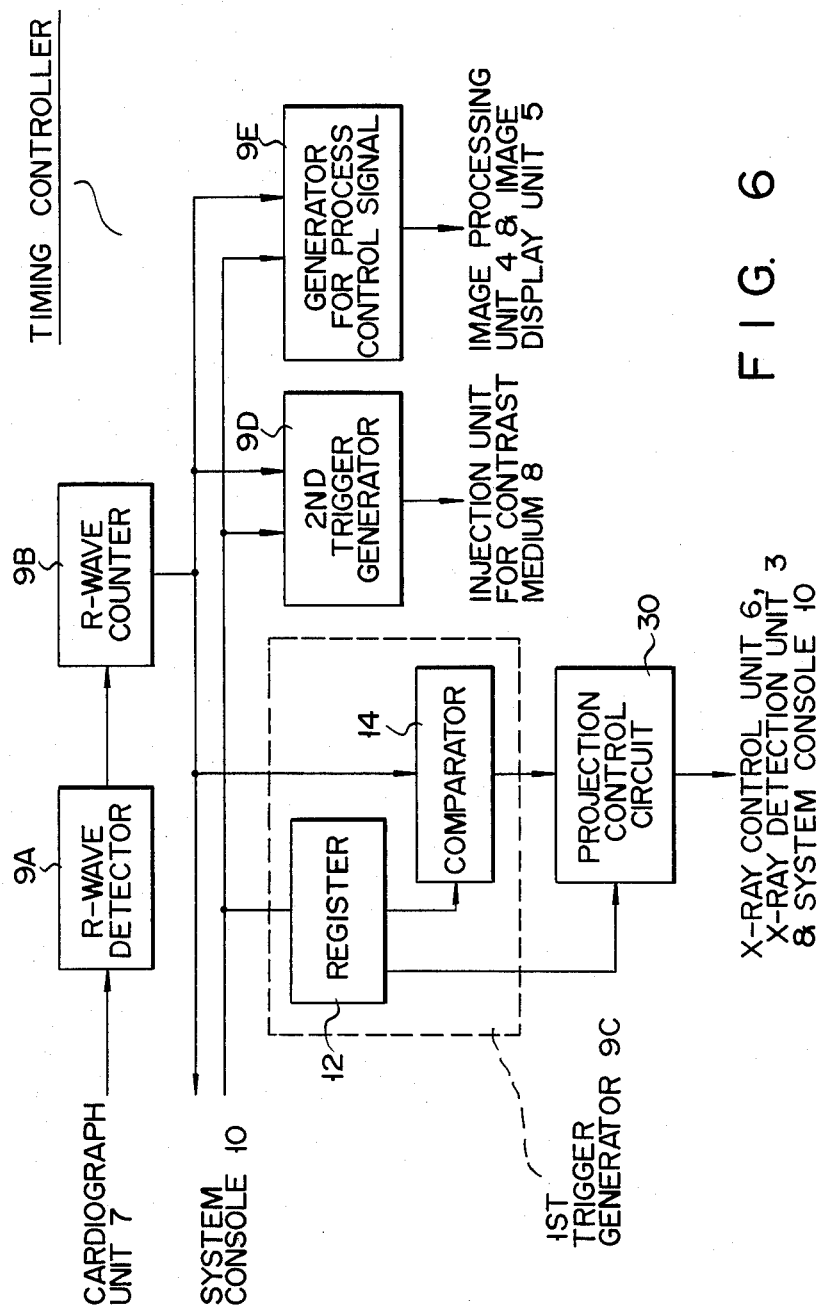
FIG. 6 is a block diagram of an internal circuit of a timing controller according to a second preferred embodiment.

A main difference between the X-ray diagnostic apparatus which projects the pulsatory X-ray and the first embodiment relates to the construction of the timing controller. Therefore, only the circuit arrangement of this timing controller will be explained hereinbelow with reference to FIG. 6. In FIG. 6, although the constructions of and interconnection among the R-wave detector 9A, R-wave counter 9B, 1st and 2nd trigger generators 9C and 9D, and generator for process control signal 9E are substantially equal to those in FIG. 2, a different point is that the output signal of the R-wave counter 9B is supplied to the system console 10. The reason for this is to average the beat number prior to project the pulsatory X-rays. A register 12 is provided in the 1st trigger generator 9C and this register 12 serves to temporarily store a pulse width of the pulsatory X-ray, a pulse repetition rate, and the delay time "$T_2$" (see FIG. 7) from the R-wave of the cardiac beat wave specified by a predetermined beat number in addition to the set pulse number supplied from the system console 10. In addition, one output terminal of the register 12 is connected to one input terminal of a comparator 14, while an output terminal of the R-wave counter 9B is connected to the other input terminal of the comparator 14. Also, the other output terminal of the register 12 is connected to a projection control circuit 30, thereby supplying the pulse width and delay time "$T_2$". An output terminal of the comparator 14 is connected to the projection control circuit 30, thereby executing the timing control of the X-ray control unit 6 and X-ray detection unit 3 in the similar manner as in the first embodiment.

In this projection control circuit 30, the maximum pulse quantities in one beat interval (i.e., one cardiac cycle) are calculated on the basis of the above-mentioned delay time, pulse repetition rate and average heat number, and further these maximum pulse quantities are displayed on the TV monitor of the system console 10.

The operator selects a proper pulse number that is smaller than the maximum pulse quantities, for example, two pulses based upon the indication on the built-in TV monitor and inputs it by the keyboard.

The operations of the pulsatory X-ray diagnostic apparatus as described above will be explained with reference to a timing chart of FIG. 7.

First of all, in the manner similar to the first embodiment, the operator inputs the beat number to determine the timing to collect images and the beat number to determine the timing to inject the X-ray contrast medium by the interactive system with the operator through the system console 10. As previously described, the cardiograph unit 7 sequentially outputs the electrocardiogram data of the object 2 as the digital signal to the timing controller 9.

Accordingly the numbers of the cardiac beat waves and the variation thereof are displayed in turn on its built-in TV monitor under control of the timing controller 9.

Then the pulse width, the delay time "$T_2$" that is measured from the R-wave defined by the given beat number, and the pulse repetition rate are input through the keyboard. When those input data are obtained in the system console 10, the maximum pulse number is calculated therein and thus displayed on the built-in TV monitor.

As described above, the appropriate pulse number, e.g., two, smaller than the maximum number of X-ray pulses is determined and this is input through the system console 10.

After it was inputted, and after the examination start command is inputted through the system console 10, the number of R-waves is started counting by the R-wave counter 9B as in the foregoing embodiment.

The number of R-waves counted by the R-wave counter 9B is supplied to the comparator 14, while the first beat number "K" which has been preset by the system console 10 is temporarily stored in the register 12. These two input signals are compared by the comparator 14. If they coincide with each other, the first trigger signal is output from the comparator 14 to the projection control circuit 30. As a result, the abovementioned predetermined processings are performed by the projection control circuit 30, so that the timing control of the X-ray control unit 6 and X-ray detection unit 3 is executed.

Subsequently, the process control signal is derived from the generator for process control signal 9E to the image processing unit 4. Accordingly, as shown in FIG. 7, for example, two pulsatory X-rays projected at every one cardiac beat from the X-ray tube 1 under control of the X-ray control unit 6 at a pulse interval $T_3$ after the delay time $T_2$ has passed from the start instant $T_1$ of the X-ray generation within the X-ray generation interval. The time instant $T_1$ is determined in that it is measured from the R-wave defined by the given cardiac beat number, e.g., "K". The pulsatory X-rays are projected, or irradiated until the time period of the delay time $T_1$ has passed from the generation instant of the first trigger signal. This trigger signal is generated when the number of R-waves counted by the R-wave counter 9B coincides with the second beat number "L" preset by the system console 10. On the other hand, the image processing unit 4 stores the images whenever the pulsatory X-rays are projected, or irradiated, and memorizes these images as a plurality of (in this embodiment, four) mask images before the X-ray contrast medium is injected.

Thereafter, the injection unit for X-ray contrast medium 8 is made operative in synchronism with the third beat number "0" in a similar manner as in the first embodiment, thereby injecting the X-ray contrast medium into the object 2.

After the contrast medium has been injected, a number of (in this embodiment, six) contrast images are obtained due to the projection of pulsatory X-rays using the fourth and fifth beat numbers "M" and "N" as the reference signals, as in the case where the mask images were stored. Thereafter, these contrast images are memorized in a memory (not shown in detail) in the image processing unit 4. Similarly hereinbelow, the image processing unit 4 produces the subtraction images from the contrast and mask images and the resulting subtraction images are displayed by the image display unit 5.

The present invention will now be summarized. According to the present invention, the number of R-waves in the electrocardiogram output from the cardiograph unit 7 is counted and when the given number of R-wave which was input by the interactive way through the system console 10 coincides with that of the counted R-wave, the trigger signal and process control signal are produced from the timing controller 9. In response to these signals, the X-rays are projected and the images obtained by the X-ray projection are stored as the video signal, and the image processing (digital subtraction) is performed between the mask and contrast images at the same phase of cardiac beat waves. Therefore, it is possible to reduce the unnecessary exposure dosage to the object under investigation, and at the same time, the diagnostic images with high picture quality can be displayed. This high quality image display enables the examiner to perform the accurate diagnosis using the apparatus for examining an biological object by radiation according to the present invention.

While the invention has been described in terms of certain preferred embodiments, and exemplified with respect thereto, those skilled in the art will readily appreciate that various modifications, changes, omissions, and substitutions may be made without departing from the spirit of the invention.

For example, in the above-described embodiments, although the R-wave of the cardiac beat waves has been used as the reference signal for the system control, it is obvious that the invention is not limited to this. As will be easily appreciated from FIG. 3, the other waves, e.g., T-wave may be used as the reference signal. In short, a prerequisite of the present invention is that a typical wave in the constitutional portion of the cardiac beat waves is extracted and this wave is used as the reference signal, and at the same time this is used as the synchronous control reference of the entire system.

Although the continuous X-ray has been projected in the first embodiment, it is not limited to this. For example, the pulsatory X-rays having a short pulse width may be continuously projected. Namely, in the present application, the continuous X-ray incorporates not only an X-ray which is projected without interruption during a predetermined time period, but also pulsatory X-rays which are continuously projected, or irradiated during the predetermined time period.

What is claimed is:

1. An apparatus for producing video difference images of an object having heart beats from X-ray images obtained from X-ray radiation passed through that object, comprising:
    means for detecting said heart beats of the object to be diagnosed;
    means for producing first video signals corresponding to a first X-ray image occurring at a predetermined phase of a first one of said heart beats;
    means for subsequently injecting said object with an X-ray contrast media;
    means for producing second video signals corresponding to a second X-ray image occurring at the same phase of a later second one of said heart beats as that of said first heart beat, delayed from said first heart beat by a predetermined number of said heart beats dependent upon the expected distribution of said X-ray contrast media within said object;
    means for subtracting said first video signals from said second video signals to produce difference video signals of said object; and
    means for displaying an X-ray image of said object corresponding to said difference video signals.

2. An apparatus for examining a biological object by using radiation comprising:
    means for generating radiation;
    means for controlling the radiation generating means so as to irradiate the radiation toward the biological object at a predetermined time period;
    means for detecting the radiation which has been transmitted through the biological object and for producing a radiation transmission image thereof as a digital image signal;
    means for processing a plurality of digital image signals in a digital subtraction method so as to obtain a plurality of subtraction image signals;
    means for displaying at least a subtraction image of the biological object obtained from the subtraction image signals;
    means for measuring cardiac beat waves of the biological object;
    means for administrating a radiation contrast medium into the biological object;
    system control means for performing at least timing controls of the apparatus in synchronism with the cardiac beat waves of the biological object as a reference signal;
    wherein:
       the radiation generating means generates X-rays;
       the detecting means produces at least a first transmission image as a mask image and a second transmission image as a contrast image in conjunction with administration of the contrast medium;
       the system control means includes a timing controller and a system console having a memory into which a predetermined timing program has been stored, whereby the timing controls of the apparatus are effected by the timing controller in synchronism with the cardiac beat waves under control of the predetermined control program;
    and further wherein:
       the X-rays are generated in the continuous condition from the radiation generating means;
       the reference signal is derived from an R-wave of the cardiac beat waves; and
       the timing controller includes:
       an R-wave detector for detecting the R-waves from the cardiac beat waves by means of a threshold level detection;
       an R-wave counter for counting the number of R-waves derived from the R-wave detector;
       a first trigger generator for generating a first trigger signal based upon the predetermined timing program and the counted number of R-waves, whereby the first trigger signal the counted number of R-waves, whereby the first trigger signal is used to control operation timings of the radiation generating means and the radiation detecting means;
       a second trigger generator for generating a second trigger signal based upon the predetermined timing program and the counted number of R-waves, whereby the second trigger signal is used to control an operation timing of the means for administrating a radiation contrast medium; and
       a generator for generating a process control signal based upon the predetermined timing program and the counted number of R-waves, whereby the process control signal is used to control operation timings of the processing means for digital image signals and the displaying means.

3. An apparatus for examining a biological object by using radiation comprising:
    means for generating radiation;
    means for controlling the radiation generating means so as to irradiate the radiation toward the biological object at a predetermined time period;
    means for detecting the radiation which has been transmitted through the biological object and for producing a radiation transmission image thereof as a digital image signal;

means for processing a plurality of digital image signals in a digital subtraction method so as to obtain a plurality of subtraction image signals;

means for displaying at least a subtraction image of the biological object obtained from the subtraction image signals;

means for measuring cardiac beat waves of the biological object;

means for administrating a radiation contrast medium into the biological object; and system control means for performing at least timing controls of the apparatus in synchronism with the cardiac beat waves of the biological object as a reference signal;

wherein:

the radiation generating means generates X-rays;

the detecting means produces at least a first transmission image as a mask image and a second transmission image as a contrast image in conjunction with administration of the contrast medium;

the system control means includes a timing controller and a system console having a memory into which a predetermined timing program has been stored, whereby the timing controls of the apparatus are effected by the timing controller in synchronism with the cardiac beat waves under the control of the predetermined control program;

and further wherein:

the X-rays are generated in the pulsatory condition from the radiation generating means;

the reference signal is derived from an R-wave of the cardiac beat waves; and the timing controller includes:

an R-wave detector for detecting the R-waves from the cardiac beat waves by means of a threshold level detection;

an R-wave counter for counting the number of R-waves derived from the R-wave detector;

a first trigger generator for generating a first trigger signal based upon the predetermined timing program and the counted number of R-waves;

a projection control circuit into which the first trigger signal is applied and also projection numbers of the pulsatory X-rays, a pulse width and a repetition time of the pulsatory X-rays are applied as the predetermined timing program from the system console and from which a projection control signal is derived so as to control operation timings of the radiation generating means and the radiation detecting means;

a second trigger generator for generating a second trigger signal based upon the predetermined timing program and the counted number of R-waves, whereby the second trigger signal is used to control an operation timing of the administrating means for contrast medium; and a generator for generating a process control signal based upon the predetermined timing program and the counted number of R-waves, whereby the process control signal is used to control operation timings of the processing means for digital image signals and the displaying means.

4. An apparatus as claimed in claim 3, wherein the first trigger generator includes a register for temporarily storing the counted numbers of the R-wave and the predetermined timing program, and a comparator for comparing the counted numbers of the R-wave to the predetermined timing program whether the counted numbers are coincident with predetermined numbers of the predetermined timing program.

* * * * *